United States Patent
Hendel et al.

(10) Patent No.: US 6,706,890 B2
(45) Date of Patent: Mar. 16, 2004

(54) METHOD FOR PRODUCING OXINDOLES

(75) Inventors: Wolfram Hendel, Leonding (AT); Ulfried Felfer, Linz (AT); Karl Schwendinger, Linz (AT)

(73) Assignee: DSM Fine Chemicals Austria Nfg GmbH & Co KG, Linz (AT)

( * ) Notice: Subject to any disclaimer, the term of this patent is extended or adjusted under 35 U.S.C. 154(b) by 98 days.

(21) Appl. No.: 10/168,848

(22) PCT Filed: Nov. 30, 2000

(86) PCT No.: PCT/EP00/12010

§ 371 (c)(1), (2), (4) Date: Jun. 26, 2002

(87) PCT Pub. No.: WO01/47884

PCT Pub. Date: Jul. 5, 2001

(65) Prior Publication Data

US 2004/0014986 A1 Jan. 22, 2004

(30) Foreign Application Priority Data

Dec. 27, 1999 (AT) .............................................. 2182/99

(51) Int. Cl.$^7$ ............................................. C07D 209/34
(52) U.S. Cl. ..................................................... 548/486
(58) Field of Search ........................................ 548/486

(56) References Cited

U.S. PATENT DOCUMENTS 5,973,165 A  10/1999  Kuo et al. ................... 548/486

OTHER PUBLICATIONS

Database HCA "Online!", Chemical Abstracts Service, Columbus, Ohio, U.S.: Abstract No. 123:285775 XP002167820 (1995).

*Primary Examiner*—Joseph K. McKane
*Assistant Examiner*—Kamal Saeed
(74) *Attorney, Agent, or Firm*—Wenderoth, Lind & Ponack, LLP

(57) ABSTRACT

The invention relates to a method for producing 2-oxindoles from the corresponding isatines of formula (I), wherein R can be H, $CH_3$, phenyl or benzyl and $R_1$ can be H, $C_1$–$C_4$-alkyl, $C_1$–$C_4$-alkoxy, phenyl phenoxy, halogen, amino, nitro or hydroxy. Said isatines are converted by means of hydrazine hydrate in a polar solvent at a temperature of 15 to 185° C. to form a corresponding isatine hydrazone which directly undergoes further reaction to form the corresponding 2-oxindole of formula (II) by adding diazabicyclooctane and/or diazabicycloundecane and/or ethyldiisopropylamine as a catalyst in temperatures of 100 to 185° C., whereby the produced reaction water is distilled off. According to formula (II), R and $R_1$ have the aforementioned definitions. The 2-oxindole is isolated from the reaction mixture by distilling off the solvent and by means of crystallisation.

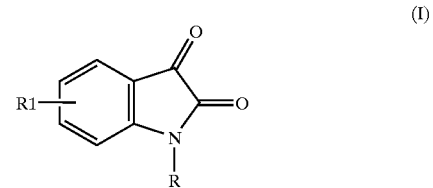

(I)

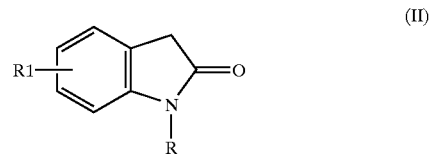

(II)

9 Claims, No Drawings

METHOD FOR PRODUCING OXINDOLES

Oxindoles are valuable intermediates in the synthesis of pharmaceutical products, such as cardiac drugs or tyrosine kinase inhibitors which regulate skin growth.

J. Chem. Educ. 1993, 70 (4), p. 332 discloses that 2-oxindoles are prepared by a two-step reaction, the first step of which comprises reacting isatin with hydrazine hydrate in anhydrous methanol to give the intermediate isatin hydrazone and isolating and purifying the intermediate. In the second step, the purified and dried intermediate is subjected to a Wolf-Kishner reduction in an anhydrous ethanol solution in the presence of a strong base such as sodium ethoxide. The yields achieved by this preparation method are up to about 69%. However, the disadvantage of this variant is the necessity of isolating, purifying and drying the intermediate before the reduction step can take place. A further disadvantage is the use of expensive, anhydrous ethanol as solvent because of the readiness of sodium ethoxide to react with water. A further preparation variant is described by Synth. Commun. 1994, 24 (20), p. 2835–41. In this variant, isatin is first dissolved in pure hydrazine and then reacted with pure hydrazine under reflux to give 2-oxindole in yields of up to 76%. However, this method requires a large quantity of pure hydrazine which serves as solvent and as reagent. When pure hydrazine is used, there is known to be a risk of explosion on heating or on reaction with oxidizing agents, so that particular safety measures have to be taken. An improvement suggested by U.S. Pat. No. 5,973,165 comprises preparing 2-oxindoles by reacting isatin with hydrazine hydrate in the presence of a weak base as catalyst and in a polar solvent. In order to obtain the desired end product in pure form, after the end of the reaction, 2-oxindole (purity about 97%) is first extracted, the extract is dried and then dissolved in a suitable solvent, and activated carbon is then added to the solution to decolorize it. After filtering off the activated carbon, 2-oxindole is crystallized out of the solution and obtained in a purity of 99.5%. The yields which are obtained by this process according to Example 1 are around 85%, but otherwise from 52 to 72%.

It is an object of the present invention to provide a process which facilitates the preparation of oxindoles in high yields and purity while avoiding complicated purification steps.

The invention accordingly provides a process for preparing 2-oxindoles of the formula (II)

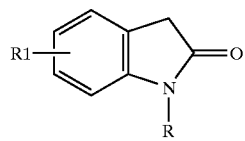

where R is H, CH$_3$, phenyl or benzyl, R$_1$ is H, C$_1$–C$_4$-alkyl, C$_1$–C$_4$-alkoxy, phenyl, phenoxy, halogen, amino, nitro or hydroxy, by reacting the corresponding isatins of the formula (I)

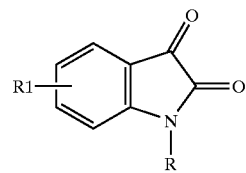

in a polar solvent with hydrazine hydrate in the presence of a tertiary amine catalyst, characterized in that the isatin is converted to the corresponding isatin hydrazone at a temperature of from 15 to 185° C. which is directly reacted further by adding a diazabicyclooctane and/or diazabicycloundecane and/or ethyldiisopropylamine catalyst a temperatures of from 100 to 185° C. while distilling off the water of reaction formed to give the corresponding 2-oxindole of the formula which is then isolated by distilling off the solvent and crystallizing out of the reaction mixture.

The process according to the invention converts an isatin of the formula (I) to the corresponding 2-oxindoles of the formula (II). The isatins used as starting compound may be substituted in the nitrogen atom by H, CH$_3$, phenyl or benzyl. Preference is given to the nitrogen atom being substituted by H. The starting compounds may also be substituted in positions 4, 5, 6 or 7 by H, C$_1$–C$_4$-alkyl, C$_1$–C$_4$-alkoxy, phenyl, phenoxy, halogen, amino, nitro or hydroxy. Preference is given to the H or OCH$_3$ substituents, and particular preference to H. The appropriate isatin is dissolved in a polar solvent as an initial charge. Useful solvents include alcohols having a boiling point above about 100° C. Examples thereof include C$_4$–C$_{10}$-alcohols such as butanol, hexanol, 2-ethylhexanol, etc. Preference is given to using hexanol or 2-ethylhexanol, more preferably 2-ethylhexanol. From a molar deficiency to a molar excess of hydrazine hydrate is then added. The quantity of hydrazine hydrate used is generally in a range from about 5% molar deficiency to a 5% molar excess. Preference is given to from a 3% molar deficiency to a 1% molar excess, and particular preference to from a 1% molar deficiency to an equimolar quantity. After the hydrazine hydrate is added, the reaction mixture is held at the reaction temperature to form the isatin hydrazone for from about 10 to 120 minutes, preferably from 30 to 100 minutes and more preferably from 40 to 80 minutes. The reaction temperatures is from 15 to 185° C., preferably from 20 to 100° C. and more preferably from 30 to 60° C.

The isatin hydrazone formed is not isolated from the reaction mixture, but is instead further processed directly. To this end, a tertiary amine catalyst is added. Examples of useful tertiary amines include diazabicyclo compounds such as diazabicyclooctane (DABCO) or diazabicycloundecene (DBU), or trialkylamines such as ethyldiisopropylamine. Preference is given to using DABCO as catalyst. The catalyst in the process according to the invention is added in a quantity of from 5 to 40 mol % based on the starting compound isatin. Preference is given to adding a catalyst quantity of from 10 to 30 mol %, more preferably from 15 to 25 mol %. The reaction temperature for this step is from 100 to 185° C., preferably from 120 to 160° C. and more preferably from 125 to 145° C. This results in nitrogen elimination. At the same time, the water of reaction resulting from the hydrazone formation is distilled off under atmospheric pressure and the reaction solution held at the reaction temperature until complete conversion. If desired, the water of reaction may already be withdrawn from the reaction mixture before the catalyst is added, for example by means of azeotropic distillation. A portion of the solvent is then distilled off to isolate the corresponding 2-oxindole. Preference is given to removing from about 50 to 90%, more preferably from about 60 to 80% of the solvent from the reaction mixture. The remaining reaction solution is slowly cooled to a temperature of from 0° C. to room temperature with stirring to crystallize the 2-oxindole. If desired, an ether such as methyl tert-butyl ether (MTSE) or diisopropyl ether (DIPE) may also be added before crystallization. The quantity added may be up to twice the quantity of the solvent remaining. The product is then filtered off, washed with the cold solvent, preferably that used in the reaction or the ether added before the crystallization, and dried.

The process according to the invention provides 2-oxindoles in high yields and high purity without requiring any complicated purification steps. Preference is given to using the process according to the invention for preparing unsubstituted 2-oxindole, which is obtained in a purity of up to 99.9 area % by GC.

EXAMPLE 1

393.3 g of isatin (2.63 mol, purity 98.2%) were initially charged into a 2 l double jacket vessel and 2000 ml of 2-ethylhexanol were added. With stirring (KPG, 250 rpm), 131 ml of hydrazine hydrate (135.2 g, 2.70 mol, purity 100.6%) were added within 15 minutes, which caused the temperature to increase from 23° C. to 45° C. and an intensely orange suspension to form. The reaction mixture was heated further and held at 90° C. for 60 minutes to form isatin hydrazone (yellow suspension). 61.2 g of DABCO (0.55 mol, 98%) were then added and the reaction solution continuously heated up to 130° C. which resulted in the onset of nitrogen cleavage above about 100° C. At the same time, the water (reaction water+hydrate water, 96.5 ml altogether) was discharged. This resulted in refluxing and foaming of the reaction mixture. The reaction mixture was held at 130° C. until complete conversion (about 4.5 h). 1500 ml of 2-ethylhexanol were then distilled off at 90–95° C. (20–30 mbar, contained 0.02% by weight of hydrazine) and the remaining reaction solution was slowly cooled to room temperature with stirring to crystallize the 2-oxindole (from 130° C. to 50° C. in 3 h, then left to stand overnight at room temperature). The crystals were filtered off, washed with 5×50 ml of cold 2-ethylhexanol (0° C.) and sucked to dryness. 509 g of damp product were obtained which was dried for about 48 hours in a vacuum drying cupboard (80–90° C. and 50–65 mbar) to constant weight. Altogether, 295 g of dry 2-oxindole product (light brown) were obtained which corresponded to an overall yield of 84.4%. The dry product was then comminuted and homogenized in a mortar.

EXAMPLE 2

400.6 g of isatin (2.72 mol, purity 98.2%) were initially charged into a 2 l double jacket vessel and 2000 ml of 2-ethylhexanol were added. With stirring (KPG, 250 rpm), 131 ml of hydrazine hydrate (135.2 g, 2.70 mol, purity 100.6%) were added within 15 minutes, which caused the temperature to increase from 23° C. to 45° C. and an intensely orange suspension to form. The reaction mixture was heated further and held at 50° C. for 60 minutes to form isatin hydrazone (yellow suspension). 61.2 g of DABCO (0.55 mol, 98%) were then added and the reaction solution continuously heated up to 130° C. which resulted in the onset of nitrogen cleavage above about 100° C. At the same time, the water (reaction water+hydrate water+2-ethylhexanol, 114.7 g altogether) was discharged. This resulted in refluxing and foaming of the reaction mixture. The reaction mixture was held at 130° C. until complete conversion (5 h). 1500 ml of 2-ethylhexanol were then distilled off at 90–95° C. (20–30 mbar, contained 0.02% by weight of hydrazine), the reaction solution was cooled to 50° C. and admixed with 732 g of MTBE and then cooled slowly with stirring to crystallize the 2-oxindole (from 130° C. to 50° C. in 3 h, then left to stand overnight at room temperature). The crystals were filtered off, washed with 3×50 ml of cold MTBE (5° C.) and sucked to dryness. 328.1 g of damp product were obtained which was dried for about 48 hours in a vacuum drying cabinet (80–90° C. and 50–65 mbar) to constant weight. Altogether, 298.7 g of dry 2-oxindole product (light brown) were obtained which corresponded to an overall yield of 83.1%.

EXAMPLE 3

40.39 g of isatin (0.27 mol, purity 98.2%) were initially charged into a 500 ml four-neck flask and 200 ml of 2-ethylhexanol were added. With stirring (KPG, 250 rpm), 13.1 ml of hydrazine hydrate (13.5 g, 0.27 mol, purity 100.6%) were added within 15 minutes, which caused the temperature to increase from 23° C. to 45° C. and an intensely orange suspension to form. The reaction mixture was heated further and held at 50° C. for 60 minutes to form isatin hydrazone (yellow suspension). Afterwards, 6.12 g of DABCO (55 mmol, 98%) were added and the reaction mixture heated for a further about 0.5 hour until the DABCO had dissolved. The suspension was then charged in portions into 35 ml of 2-ethylhexanol in a receiver vessel which had been preheated to 145–150° C. Since addition of the cold suspension to the preheated 2-ethylhexanol resulted in an immediate temperature decrease which slowed the nitrogen elimination, the isatin hydrazone suspension was added in portions of each about 5 ml at intervals of 2–3 min to avoid this, so that the temperature in the receiver could be maintained in the target range of 140–145° C. Occasionally, an extension of the interval of up to 5 min was necessary. During the metering in (1.5–2 h), the reaction suspension foamed vigorously, particularly at the end of the reaction. During the nitrogen elimination, about 6.5 g of a biphasic mixture of water and some 2-ethylhexanol were distilled off. In this distillate 1, no hydrazine was found. The reaction mixture was held until complete conversion (about another 1.5 hours) at 140–145° C. (IPC control, GC: complete consumption of the hydrazone at 0.1–0.2 area %). 185 ml of 2-ethylhexanol were then distilled off at 90–95° C. (20–30 mbar, contained 0.02% by weight of hydrazine). The reaction solution was cooled to 55° C. and 80 g of MTBE were added. The reaction solution was cooled to 5° C. (in 0.5–1 h, then left to stand overnight at RT) to crystallize the 2-oxindole. The crystals were filtered off, washed with 3×5 ml of cold MTBE (0° C.) and sucked to dryness. 30.0 g of damp product were obtained which were dried for about 48 hours in a vacuum drying cupboard (80–90° C. and 50–65 mbar) to constant weight. Altogether, 23.9 g of dry 2-oxindole product (light brown) were obtained which corresponded to an overall yield of 66.5%.

GC purity:

2-oxindole 99.8–99.9 area %

Impurities <0.1 area %

EXAMPLE 4

14.8 g of isatin (99 mmol, 98.2% purity) were initially charged into a 250 ml three-neck flask and 150 ml of 2-ethylhexanol were added. 6.0 g of hydrazine hydrate (117 mmol; 98% purity) were added with stirring. The reaction mixture was heated to 90° C. for 15 min to form the isatin hydrazone (yellow suspension). The water of reaction was azeotropically removed at 90° C./100 mbar using 1-hexanol. 2.4 g of DABCO (21 mmol, 98%) were then added and the suspension heated to 130° C. for 2.5 h. After the end of the reaction (GC analysis: hydrazone 0.3 area %), 100 ml of 1-hexanol were distilled off (80° C./50 mbar). The remaining solution was cooled to 5° C., the precipitated solid filtered off and dried in a vacuum drying cupboard at 70° C. Altogether, 8.0 g of dry 2-oxindole product (light brown) were obtained which corresponded to an overall yield of 66.5%. Purity: 99.9 area %.

What is claimed is:

1. A process for preparing 2-oxindoles of the formula (II)

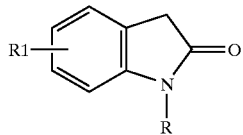

where R is H, $CH_3$, phenyl or benzyl, $R_1$ is H, $C_1$–$C_4$-alkyl, $C_1$–$C_4$-alkoxy, phenyl, phenoxy, halogen, amino, nitro or hydroxy, by reacting the corresponding isatins of the formula (I)

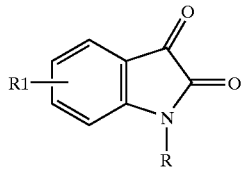

in a polar solvent with hydrazine hydrate in the presence of a tertiary amine catalyst, characterized in that the isatin is converted to the corresponding isatin hydrazone at a temperature of from 15 to 185° C. which is directly reacted further by adding a diazabicyclooctane and/or diazabicycloundecane and/or ethyldiisopropylamine catalyst at temperatures of from 100 to 185° C. while distilling off the water of reaction formed to give the corresponding 2-oxindole of the formula which is then isolated by distilling off the solvent and crystallizing out of the reaction mixture.

2. The process as claimed in claim 1, characterized in that the isatin of the formula (I) where R is H and $R_1$ is H or $OCH_3$ is converted to the corresponding 2-oxindole of the formula (II).

3. The process as claimed in claim 1, characterized in that the polar solvent used is hexanol or 2-ethylhexanol.

4. The process as claimed in claim 1, characterized in that hydrazine hydrate is added in from a 5% molar deficiency to a 5% molar excess, based on the isatin of the formula (I).

5. The process as claimed in claim 1; characterized in that the reaction temperature for forming the isatin hydrazone is from 20 to 100° C.

6. The process as claimed in claim 1, characterized in that the tertiary amine is used in a quantity of from 5 to 40 mol % based on the isatin of the formula (I).

7. The process as claimed in claim 1, characterized in that the water of reaction is already removed from the reaction mixture by azeotropic distillation before the catalyst is added.

8. The process as claimed in claim 1, characterized in that the 2-oxindole of the formula (II) is isolated by distilling off from 50 to 90% of the solvent and cooling the remaining reaction solution to crystallize the 2-oxindole of the formula (II) which is then filtered off, washed and dried.

9. The process as claimed in claim 8, characterized in that an ether is added to the reaction mixture before crystallization.

* * * * *